United States Patent
Lucia et al.

(10) Patent No.: US 6,573,512 B1
(45) Date of Patent: Jun. 3, 2003

(54) ANALYSING DEVICE NON-DESTRUCTIVE OF PLANTS AND VEHICLE COMPRISING SUCH DEVICE ON BOARD

(75) Inventors: Alfredo Lucia, Osmate (IT); Francine Heisel, Strasbourg (FR); Alphonse Martz, Kilstett (FR); Joseph-Albert Miehe, Strasbourg (FR); Jean-Pierre Oberlin, Garrebourg (FR); Malgorzata Sowinska, Ittenheim (FR); Martin Zurn, Ispra (IT)

(73) Assignee: Communaute Europeene, Luxembourg (LU)

( * ) Notice: Subject to any disclaimer, the term of this patent is extended or adjusted under 35 U.S.C. 154(b) by 0 days.

(21) Appl. No.: 09/582,104
(22) PCT Filed: Dec. 21, 1998
(86) PCT No.: PCT/FR98/02811
   § 371 (c)(1),
   (2), (4) Date: Jan. 18, 2001
(87) PCT Pub. No.: WO99/32876
   PCT Pub. Date: Jul. 1, 1999

(30) Foreign Application Priority Data

Dec. 22, 1997 (LU) .................................................. 90186

(51) Int. Cl.[7] ............................................. G01N 21/64
(52) U.S. Cl. .................................. 250/458.1; 250/461.1
(58) Field of Search ..................... 250/458.1, 459.1, 250/461.1, 461.2; 356/317, 318, 417

(56) References Cited

U.S. PATENT DOCUMENTS

| | | | | |
|---|---|---|---|---|
| 4,421,772 A | * | 12/1983 | Munck et al. .................. 241/9 |
| 4,650,336 A | * | 3/1987 | Moll ........................ 250/458.1 |
| 4,786,813 A | * | 11/1988 | Svanberg et al. ......... 250/458.1 |
| 5,130,545 A | | 7/1992 | Lussier |
| 5,682,244 A | * | 10/1997 | Barlow et al. ........... 250/458.1 |
| 5,784,157 A | * | 7/1998 | Gorfinkel et al. ........... 204/452 |
| 5,822,068 A | * | 10/1998 | Beaudry et al. ......... 250/458.1 |
| 5,960,104 A | * | 9/1999 | Conners et al. ............. 144/402 |
| 5,981,958 A | * | 11/1999 | Li et al. ................... 250/459.1 |

FOREIGN PATENT DOCUMENTS

| | | | |
|---|---|---|---|
| EP | 0 128 312 | 12/1984 | |
| EP | 128312 A2 | * 12/1984 | ........... G02B/23/16 |

OTHER PUBLICATIONS

By H. Edner et al., "Fluorescence Lidar Multicolor Imaging of Vegetation", *Applied Optics*, vol. 33, No. 13, May 1994, pp. 2471–2479.

By G. Schmuck et al., "Laser–Induced Time–Resolved Fluorescence of Vegetation", *IEEE Transactions on Geoscience and Remote Sensing*, vol. 29, No. 4, Jul. 1991, pp. 674–678.

By L. Ning et al., "Imaging Fluorometer to Detect Pathological and Physiological Change in Plants", *Applied Spectroscopy*, vol. 49, No. 10, Oct. 1995, pp. 1381–1389.

* cited by examiner

Primary Examiner—Constantine Hannaher
Assistant Examiner—Albert Gagliardi
(74) Attorney, Agent, or Firm—Young & Thompson (57) ABSTRACT

A device for non-destructive analysis of plants includes a unit transmitting a calibrated excitation laser beam, a unit measuring and imaging the fluorescence emitted by the irradiated plant(s) and a unit for digitally processing, storing and editing or displaying the collected images. The transmitting unit provides at least two different laser excitation wavelengths simultaneously and the measuring and imaging unit includes a unit for forming, from a common fluorescence beam emitted by the plant(s), simultaneously or successively, at least two secondary beams, each having its own wavelength and each constituting a fluorescence image at a matrix sensor, over the whole surface thereof or over part of the surface thereof, each image being separate for each secondary beam.

11 Claims, 10 Drawing Sheets

ANALYSING DEVICE NON-DESTRUCTIVE OF PLANTS AND VEHICLE COMPRISING SUCH DEVICE ON BOARD

BACKGROUND OF THE INVENTION

The present invention relates to the field of study of vegetation, more particularly plants, in the field of forestry and agriculture, and has for its object a device for non-destructive analysis of plants, as well as an analysis vehicle comprising such a device on board.

So as to optimize the exploitation of agricultural and forest services, it is essential to be able to determine the limit factors of the growth of the plants and to detect as soon as possible the appearance of undesirable factors.

Thus, so as to study and quantify the influence of deficiencies, hydric stresses and maladies of parasitic origin in vegetation, various types of analyses are at present known and generally carried out in a laboratory after removing specimens from the plants to be studied.

However, these extraneous analyses do not permit taking account of the environment of the plant in question, requiring complicated and fastidious removals and processing, permitting the study of only certain portions of a plant (for plants of large size) or of certain plants at the periphery of a field, which can lead to the destruction of the plant in question and do not give immediate on site results adapted to orient in place the ultimate analyses by the selection of certain plants or portions of plants, as a function of previous results.

The need for a non-destructive analysis, carried out remotely and performed on plants such as are present in their natural media (food supply, exposure to wind and sun, orientation and the like), has been apparent for a number of years.

Moreover, the principle of measuring by fluorescence is known, which consists in acquiring optically the image of the fluorescence of the vegetation, particularly the leaves, induced by a short luminous excitation, from a laser beam projected on these.

There already now exist several devices which permit carrying out measurements to extract information by the method of induced fluorescence of vegetation.

Thus, there is known for example:

from the document "Plant Efficiency Analyzer" of HANSATECH, the general principle of measuring by fluorescence of the plants, as well as the results which can be derived therefrom. Moreover, this document discloses an apparatus permitting measuring on a leaf the luminous emission produced after excitation by electroluminescent diodes, the measurement being carried out over a small surface by a photodiode;

from the document J. Plant Physiol., Vol. 148, pages 632 to 637, 1996, "Remote Fluorescence Measurements of Vegetation Spectrally Resolved and by Multi-Colour Fluorescence Imaging", JONAS JOHANSSON et al., a device for remotely measuring by laser fluorescence and recovery of images produced by fluorescence at different wavelengths. In this document, the fluorescence is measured over all no matter what the region of interest in the image, by interposition of a spectrophotometer which sweeps the different wavelengths successively and a second path permits acquisition of two simultaneous images at two different frequencies.

from the document Aust. J. Plant Physiol., 1994, 22, pages 277 to 284, "Quantitative Mapping of Leaf Photosynthesis using Chlorophyll Fluorescence Imaging", Bernard Genty et al., there is known a device for measuring by fluorescence the photosynthesis of a leaf, after removing it from its environment, by a measuring device in a laboratory, the system described not being adapted for overall on site measurement.

However, the known devices mentioned above do not give sufficient information to permit precise analysis and establishment of a diagnosis after a single measuring session, and none of these known devices is adapted to carry out, with the same device, an overall on site measurement and a measurement of a particular specimen.

Moreover, none of these devices permits entirely avoiding parasitic luminosity, nor parasitic influences generated by its control means.

Finally, none of these known devices provides a device of simple and easily transportable structure for on site measurements.

SUMMARY OF THE INVENTION

The invention particularly has for its object to overcome one or several of these drawbacks of the known devices mentioned above.

To this end, the invention has for its object a device for the non-destructive analysis of plants, and more generally of vegetation, by measurement of the fluorescence induced by laser excitation, comprising a unit for the emission of a calibrated excitation laser beam, a unit for measuring and taking images of the fluorescence emitted by the irradiated plant or plants and a digital processing unit, for storing and editing or visualizing the collective images, associated with a computer unit for the control and management of the operation of the device, which device is characterized in that the emission unit supplies at least two excitation laser wavelengths and in that the unit for measuring and collecting images comprises means to form, from a single beam of fluorescence emitted by the plant or plants simultaneously or successively, at least two secondary beams, each having its own wavelength and each constituting a fluorescent image in a matrix sensor, over all the surface of this latter (successive acquisition of images) or a portion of the surface of this latter, separately for each secondary beam (simultaneous acquisition of images).

The invention also has for its object a vehicle for the on site analysis of plants and, more particularly of vegetation, characterized in that it comprises at least one analysis device as mentioned above, mounted in a manner to be oriented and inclined on a telescoping beam.

BRIEF DESCRIPTION OF THE DRAWINGS

The invention will be better understood from the following description, which relates to a preferred embodiment, given by way of non-limiting example, and explained with reference to the accompanying schematic drawings, in which.

DESCRIPTION OF THE PREFERRED EMBODIMENTS

Figure 1:
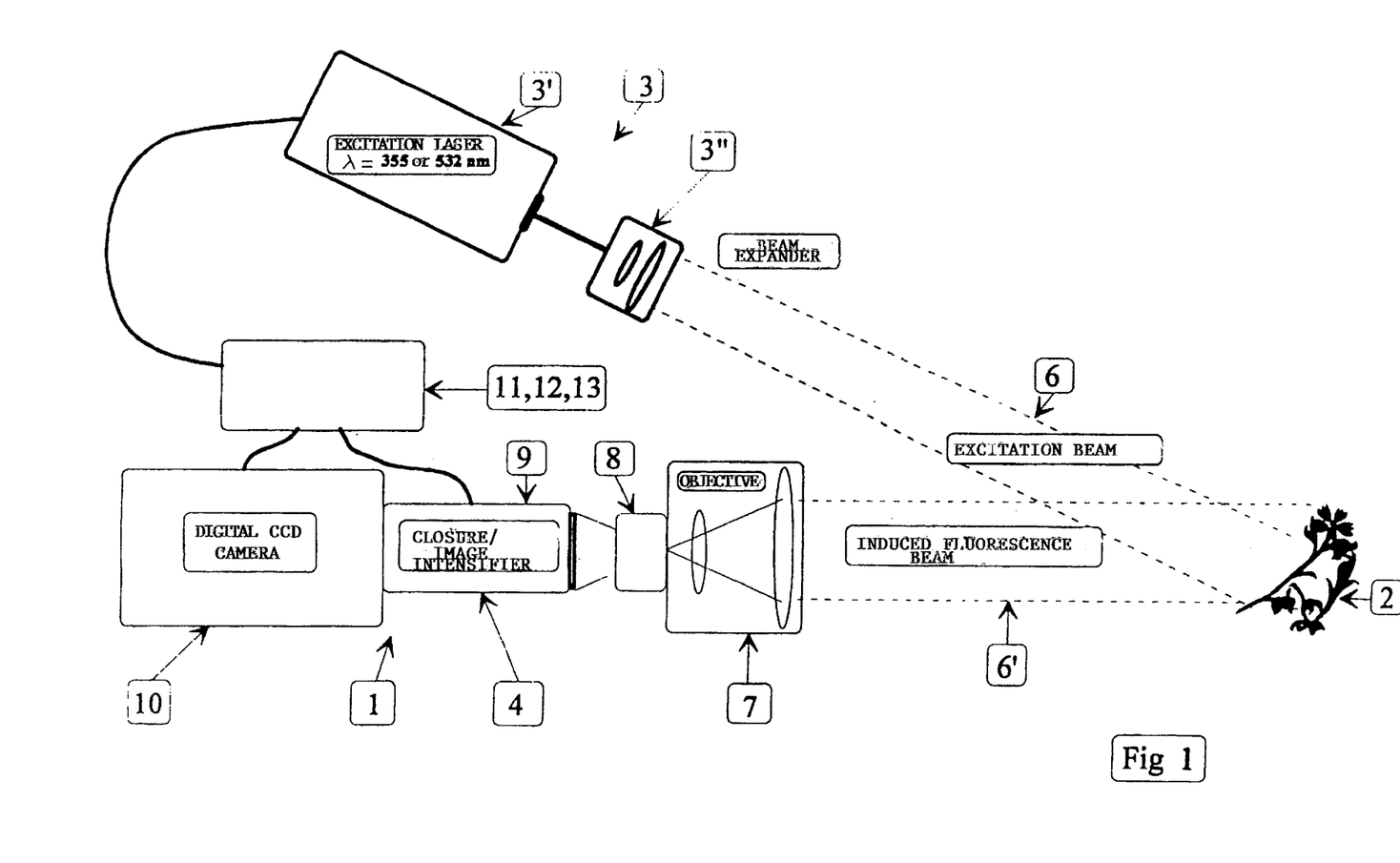
FIG. 1 is a schematic view of an analysis device according to the invention.
Figure 3:
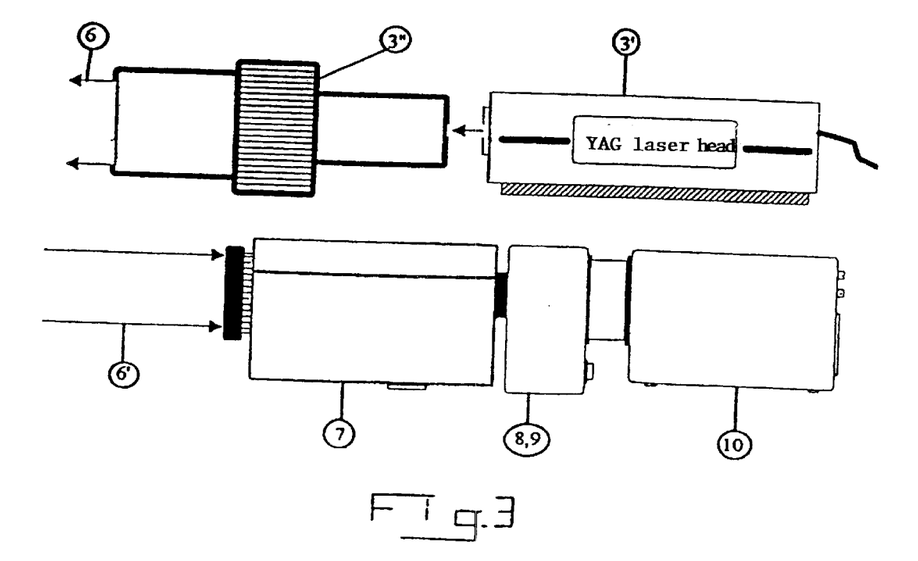
FIG. 3 is a schematic view showing the different constituent elements of the device according to the invention.

As shown in FIGS. 1 and 3 of the accompanying drawings, the non-destructive analysis device for plants, and more generally of vegetation, by measurement of fluorescence induced by an excitation laser, comprises a unit 3 for emitting a calibrated excitation laser beam 6, a unit 4 for measuring and gathering images of the fluorescence emitted by the irradiated plant or plants 2, and a digital processing unit, for storing and editing or visualizing the collected images, associated with a computer unit for controlling and managing the operation of the device 1.

According to the invention, the emission unit 3 simultaneously supplies at least two excitation laser wavelengths and the unit 4 for measuring and gathering images comprises means 7, 8, 9 to form, from a same fluorescence beam 6' emitted by the plant or plants 2, simultaneously or successively, at least two secondary beams, each having its own wavelength and each constituting a fluorescence image in a matrix sensor 10, over all of the surface of this latter (successive acquisition of images) or over a portion of the surface of this latter, separate for each secondary beam (simultaneous acquisition of images).

The multiple data supplied by this parallel or successive acquisition of images under identical external conditions, but using parameters of laser irradiation and processing of the returning optical beam different for each image, will permit, by comparison with data or reference images (collected during programming tests and preliminary programming) or by mutual comparison between them (for example: ratio of the intensities of the different wavelengths from the vegetation), analyzing the condition of the vegetation studied and diagnosing, evaluating and quantifying the condition of stress, deficiencies, parasitic invasions or other possible deficiencies of said vegetation.

According to a first embodiment of the invention, the means 8 of FIG. 1 comprise several interference filters (at least two and preferably four) mounted on a filter carrier in the form of a disk whose motor-driven movement in rotation, controlled by the computer unit for control and management, brings the different filters within the luminous path of the beam of fluorescence 6'.

According to a second embodiment of the invention, suitable for simultaneous acquisition of images, the means 8 comprises elements to divide the fluorescence beam 6' into at least two, preferably four, secondary beams of different wavelengths of which each is directed toward a zone of the matrix sensor 10 with which it is particularly concerned.

These secondary beams are therefore, simultaneously or successively, processed each by one of the interference filters 8 and the gathered collected images by the unit 4 mentioned above, for example, taken at four different wavelengths which correspond to the maxima of the blue-green fluorescence at 440 nm and 520 nm (F440 and F520) and of the chlorophylic fluorescence at 690 nm and 740 nm (F690 and F740), the beam 6 of the excitation laser preferably emitting in the ultraviolet preferably from 380 nm to 390 nm, and in the green, preferably from 560 nm to 600 nm.

Excitation in the green will permit on the one hand a greater depth of penetration and on the other hand a more direct excitation of the chlorophyll, whilst blue excitation will give not only the data on blue and green fluorescence but also on the efficacy of energy transfer toward the chloroplasts.

So as to improve the ratio of effective fluorescence signal/ambient light noise, it is provided that the durations of the sequences of opening of the assembly 9 of the closure/light intensifier, forming a part of the unit 4 for measurement and gathering images, and the duration of the laser pulses of the emission unit 3, will be correlated among themselves and that the functions of the matrix sensor 10, of the laser device 3' of the emission unit 3 and of the assembly 9 of the obturator/light intensifier, will be synchronized among themselves by means of a dedicated circuit in a corresponding loop.

This arrangement permits avoiding electromagnetic disturbances conventionally induced in optical matrix sensors 10 of the CCD type (charge coupled circuit) by switching fronts of the voltage impulses controlling the light intensifier tube adjacent to said sensors.

By way of example, the time of opening the obturator/light intensifier assembly can preferably be about 30 nanoseconds for a mid-height width of the laser pulses of 10 nanoseconds.

Figure 2:
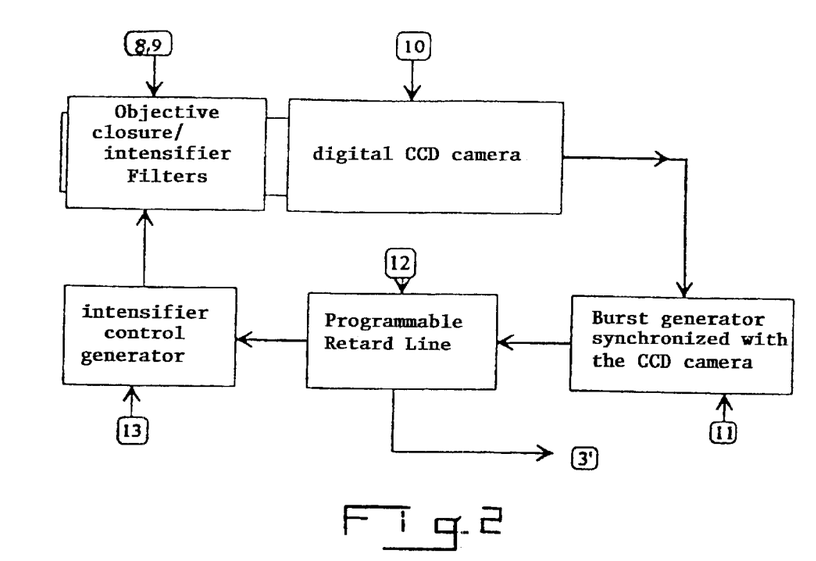
FIG. 2 is a schematic view of the synchronization loop forming a portion of the device shown in FIG. 1.

As shown in FIG. 2 of the accompanying drawings, the synchronization or loop slave circuit is constituted, on the one hand, by a burst signal generator 11, triggered by the CCD camera forming the matrix sensor 10 and controlled by the computer unit for controlling and managing, on the other hand, by an adjustable retard line 12 ensuring the transmission of said signals in bursts, particularly toward the input for triggering the laser device 3', and, finally, a module 13 for triggering the assembly 9 of the obturator/light intensifier, receiving the signals in bursts, transmitted by the retardation line 12 with a time offset determined relative to the laser device 3', said offset being a function of the distance between the device 1 and the plant or plants or region of vegetation to be analyzed, if desired measured with the help of a telemeter.

The triggering of the burst signal generator 11 is preferably operated by the signal delivered by the composite video output CCIR of the CCD camera forming a matrix sensor of 512×512 pixels, for example, divided into four image zones of 256×256 pixels, permitting the accumulation, the digitizing and memorization of the fluorescence induced in the vegetation to be analyzed at four different wavelengths, under the same conditions of excitation and illumination.

So as to eliminate the effect of movement of the vegetation or the plants to be analyzed and to avoid the consequences of fluctuations of ambient light between the acquisition period (with laser excitation) and the period of subtraction of the ambient light due to solar exposure, the images of fluorescence adapted to be used are obtained by summation of a plurality of timed images which each results from the subtraction of two images of raw fluorescence obtained during two phases of consecutive opening of the assembly 9, a first with excitation laser and a second without excitation laser.

Thus, the first image of raw fluorescence is obtained, by the fluorescent emission resulting from an excitation laser and the excitation by the sunlight and the second image of raw fluorescence is obtained by the emission of fluorescence resulting from the single excitation by the sunlight, each intermediate timed image constituting an image of fluorescence resulting solely from excitation by the laser.

Figure 12:
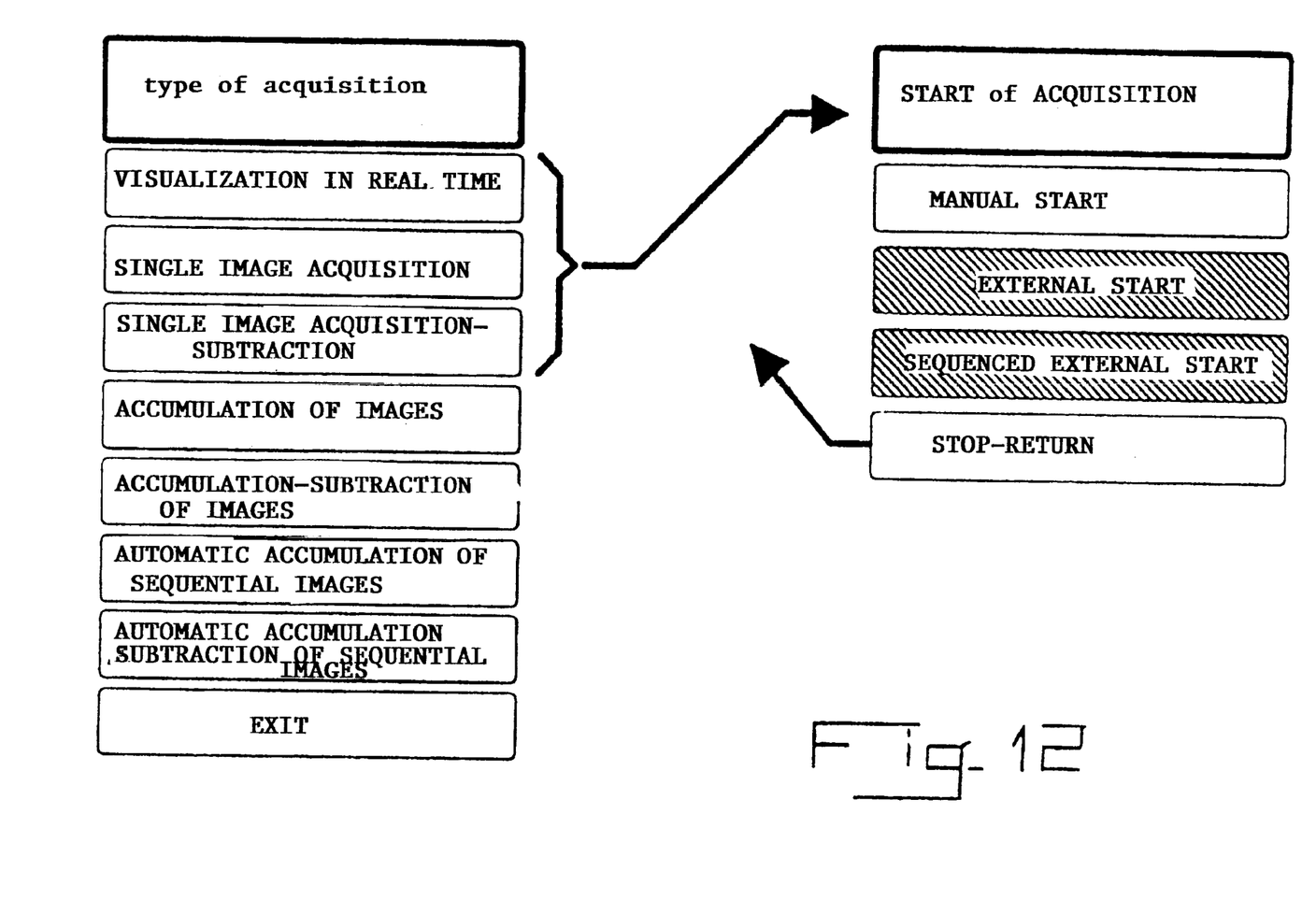
Figure 13:
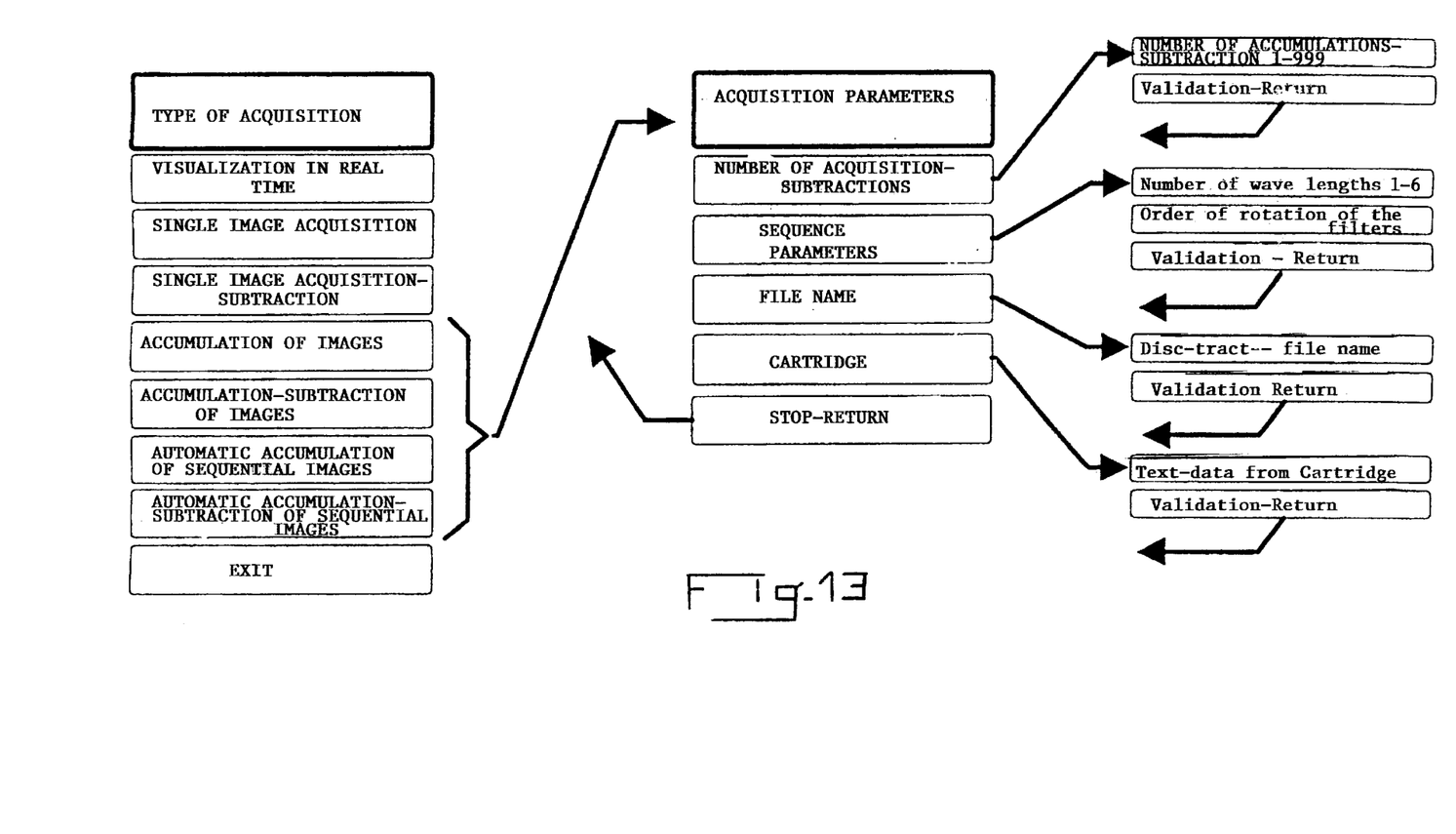
Figure 14:
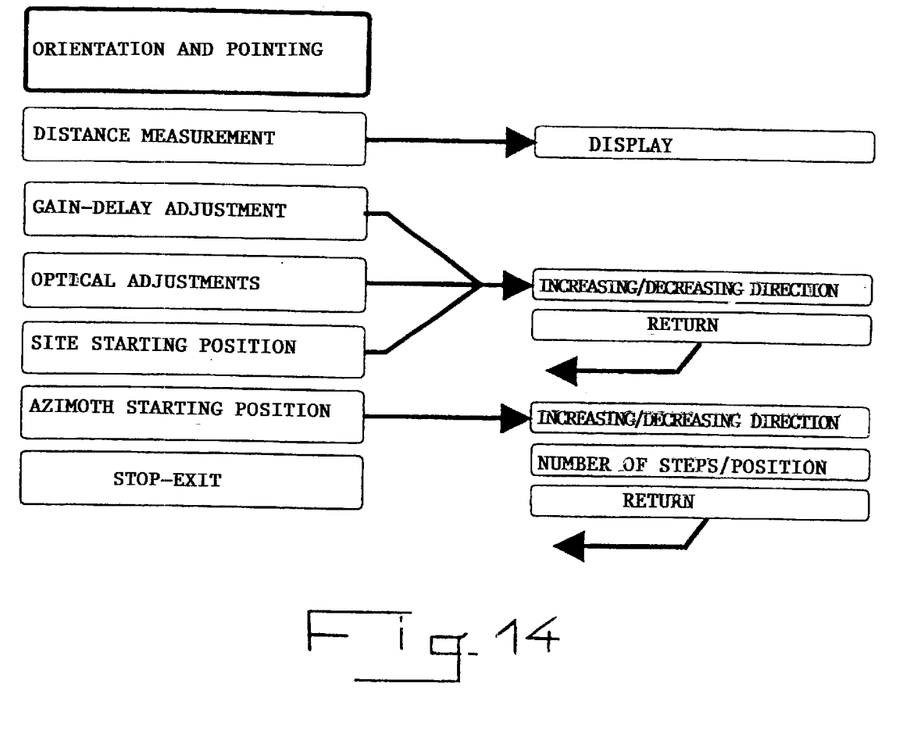

FIGS. 12 to 14 show certain procedures for programming and setting the analysis device according to the invention, the assembly of these procedures being adapted to be executed by the operator within the computer by means of interfaces of the screen, keyboard, mouse type or the like.

The different software that could be used could for example be accessible by a selection program or "principal menu" permitting accessing, by validation, with various options corresponding particularly to the possibilities of the choice of type of acquisition, of programming the acquisition, of re-reading and visualizing previous acquisitions, of orientation and pointing of the analysis device and triggering a programmed acquisition.

By way of example, FIG. 12 of the accompanying drawings shows the possibilities of the programming sequence in the case of a simple acquisition without storing, FIG. 13 shows the possibilities and the programming sequence in the case of multiple acquisitions or in sequences with storing, and FIG. 14 shows the programming sequence for physical initialization and adjustment of the analysis device 1.

Figures 4, 4A:
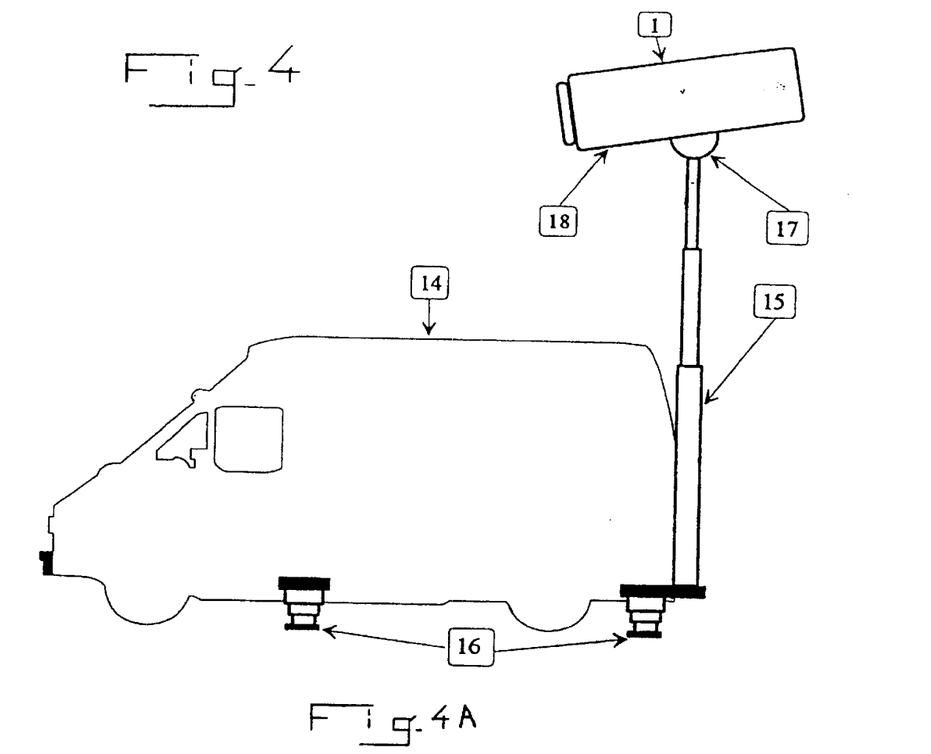
FIGS. 4A and 4B are side elevational views of an analysis vehicle according to the invention, with the analysis device respectively in an external analysis position and in a position for analysis of a specimen within the vehicle also forming a part of the invention.
Figure 4B:
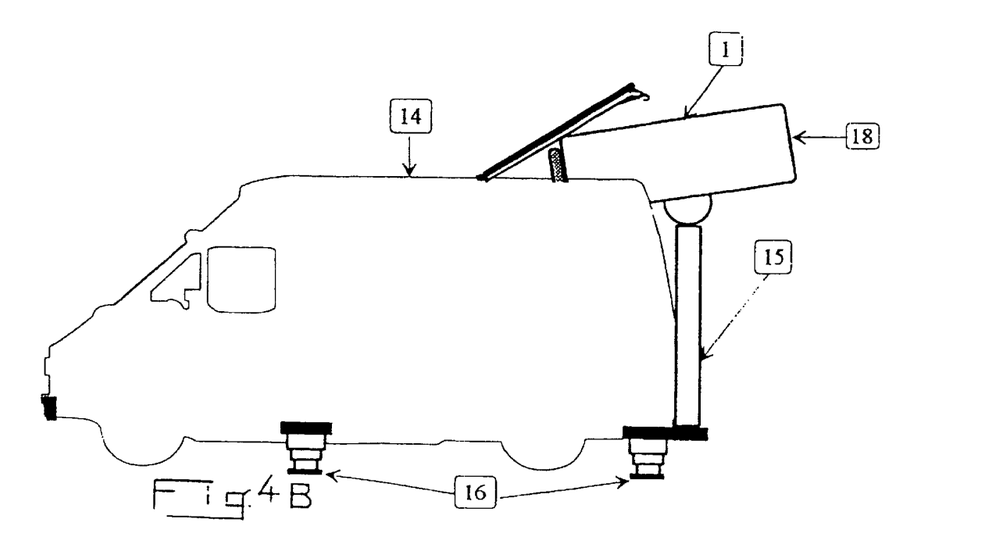

The present invention also has for its object a vehicle for the on site analysis of plants and more generally of vegetation, characterized in that it comprises at least one analysis device as described above, mounted in orientable and inclinable manner on a telescoping beam 15 (FIGS. 4A and 4B).

The mounting of the analysis device 1 on the vehicle 14 renders it mobile and transportable. The internal space of this laboratory vehicle 14 is preferably divided into two compartments, of which one is reserved for the operator of the digital processing unit, for storage and editing and/or visualizing the images associated with the computer unit for control and management and of which the other is provided for storage of measuring equipment (internal and transport measurements).

A mobile electrical generating unit, also carried by the vehicle 14, is deposited on the ground during measurements and ensures the electrical energy requirements of the assembly of the analysis device 1.

Moreover, stabilization jacks 16 can ensure the levelling of the vehicle 14 during measurement operations.

The different elements comprising the emission unit 3 (laser device 3', beam enlarger 3") and the unit for measuring and taking images 4 (objective 7, if desired a beam divider, interference filters 8, assembly 9 of obturator/light intensifier, CCD camera 10) are preferably of small size and adapted to resist abrupt accelerations without damage.

Moreover, said components of the emission unit 3 and of the unit 4 for measuring and collecting images are mounted on a beam platform or nacelle 17 that can be oriented, forming two parallel structural assemblies on lines located in an air conditioned chamber 18.

This latter is provided on its forward surface with an open inlet window and is provided with a connection line to the vehicle 14 for the circulation of fluids and electrical energy toward the nacelle 17, the pumping of the laser by fiber optics and the transfer of the returned information as to position and digital images collected by the CCD camera 10.

The size of the excitation laser beam 6 can be increased by a beam enlarger 3" provided for example to cover a circle of a diameter 0.30 m at a distance of 30 meters. The CCD camera 10 as well as the image intensifier device are oriented so as to take fluorescent images of identical surfaces, merged with the irradiated zone.

An optical range finder can complete the mentioned equipment so as to be able to measure precisely the distance between the vegetation and the equipment of the measuring head (instrumentation). It is from these data that the optical adjustments are carried out as well as the adjustment of the electronic delay (synchronization) which will permit opening the closure and the illumination intensifier.

As shown in FIGS. 4A and 4B of the accompanying drawings, the vehicle 14 is provided with a trap and the nacelle 17 carried by the beam 15 is displaceable and orientable such that the analysis device 1 can be moved between an on site analysis position of the plants 2 disposed about the vehicle 14, and an analysis position of a sample of a plant 2 taken from the adjoining region emplaced in a specimen carrier within the vehicle 14.

By way of illustrating the possibilities of the analysis device 1 according to the invention, there will be described hereafter different results of analysis of various types of portions of plants 2, with reference to FIGS. 5 to 11.

Although the preferential excitation laser wavelengths are comprised, on the one hand, between 380 nm and 390 nm and, on the other hand, between 560 nm and 600 nm, the inventors have used, to carry out their analyses, excitation wavelengths of 355 nm and 532 nm (available material).

Those skilled in the art will understand that by using the preferred wavelengths indicated, the results obtained are better than those appearing in FIGS. 5 to 11.

Figure 5:
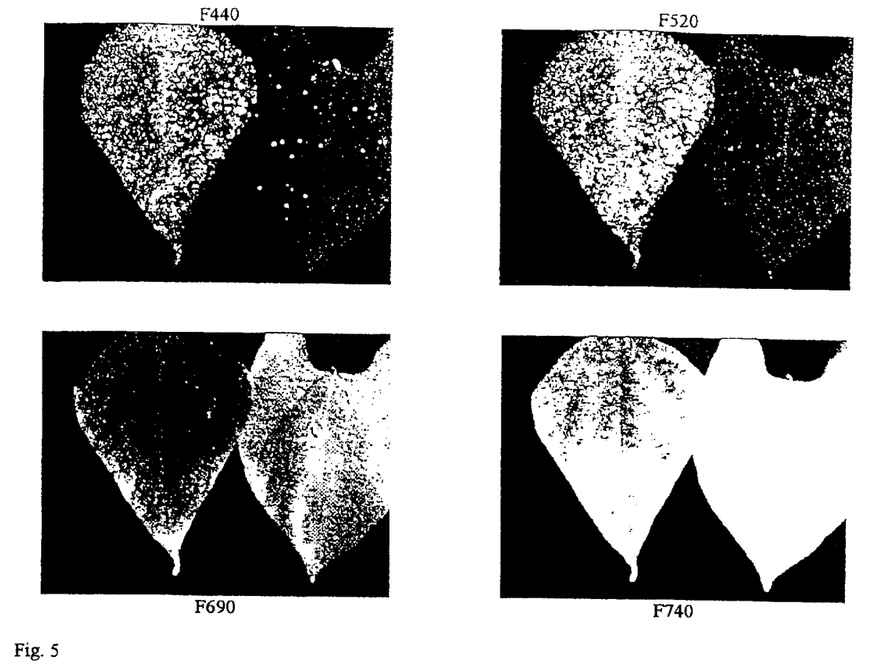
FIGS. 5 to 11 show images obtained by means of the analysis device according to the invention by fluorescence induced in plant portions, and, FIGS. 12 to 14 show examples of organic grams of execution algorithms of certain functions of the analysis device according to the invention.

FIG. 5 shows fluorescence images obtained from leaves of green beans with an excitation laser of 355 nm and collected and four emission wavelengths characteristic of the plants (F440=440 nm, F520=520 nm, F690=690 nm, F740=740 nm).

In each image, the right leaf is healthy and the left leaf is contaminated by a pathogenic agent (in this case red spiders—invisible to the naked eye).

It will be seen that on the images F440 and F520, the contaminated leaf has a characteristic fluorescence motif (small white spots) and more intense fluorescence than that of the healthy leaf. By contrast, the chlorophyll fluorescence (F690 and F740) of this same leaf is substantially weaker and less characteristic.

Figure 6:
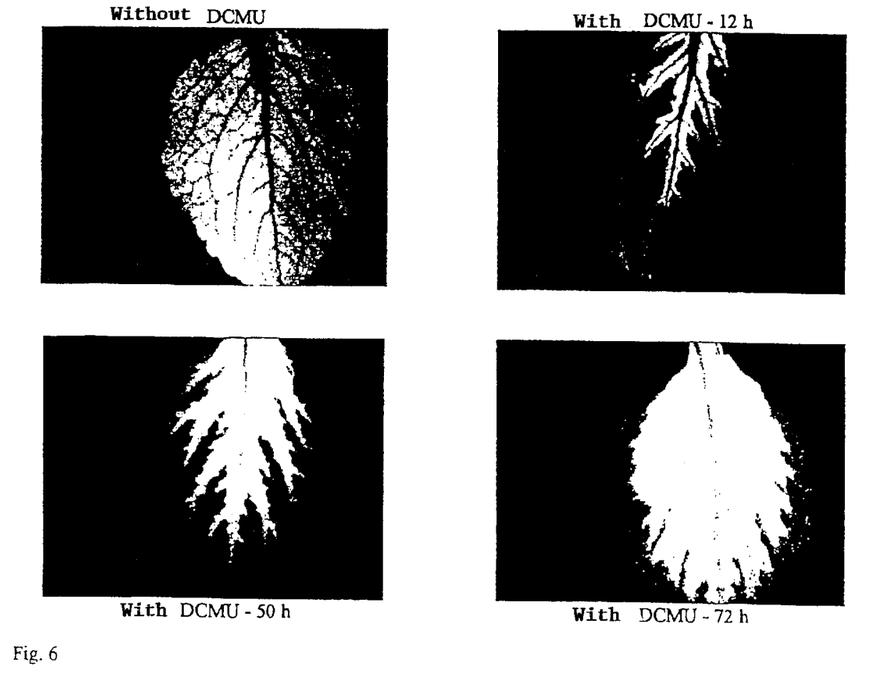

FIG. 6 shows fluorescence images obtained from a leaf of Digitalis Purpurea, subjected to treatment by herbicide (DCMU: 3-(3,4 Dichlorophenyl-1,1-dimethylurea) by the roots.

The four images of this figure have been collected at a wavelength of 690 nm with an excitation laser of 355 nm and at different intervals of time after spraying the plant with a solution of DCMU diluted ($10^{-5}$M).

As is observed nicely on these images, the different stages of diffusion through the veins of the DCMU solution over all the surface of the leaf as a function of elapsed time.

Figure 7:
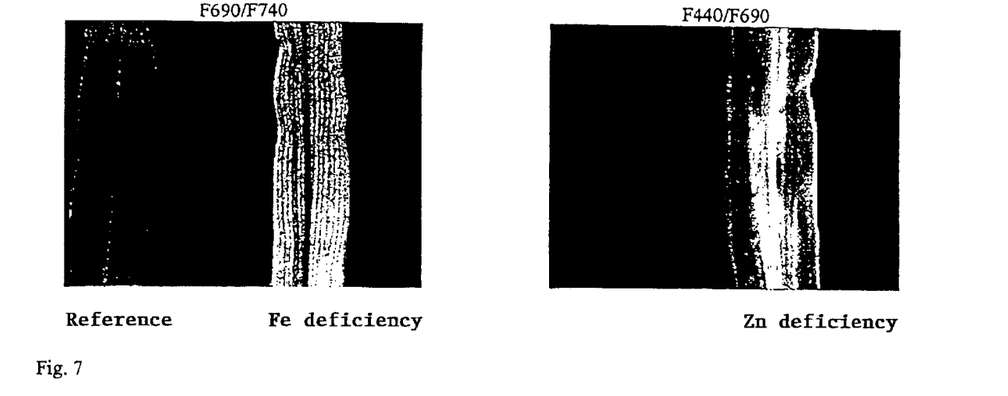

FIG. 7 shows images obtained by making the pixel-to-pixel ratio of two fluorescent images from corn leaves, respectively in good health (reference), deficient in iron and deficient in zinc.

These images were obtained at the indicated wavelengths with an excitation laser of 355 nm.

It will be noted that on the corn leaf deficient in iron, striations parallel to the central rib and on the leaf deficient in zinc large spots without apparent striations, while the image of the healthy leaf has no apparent heterogeneity.

It will also be noted that to the naked eye the striations are visible on the healthy leaves and deficient leaves and accordingly do not permit characterizing these latter.

Figure 8:
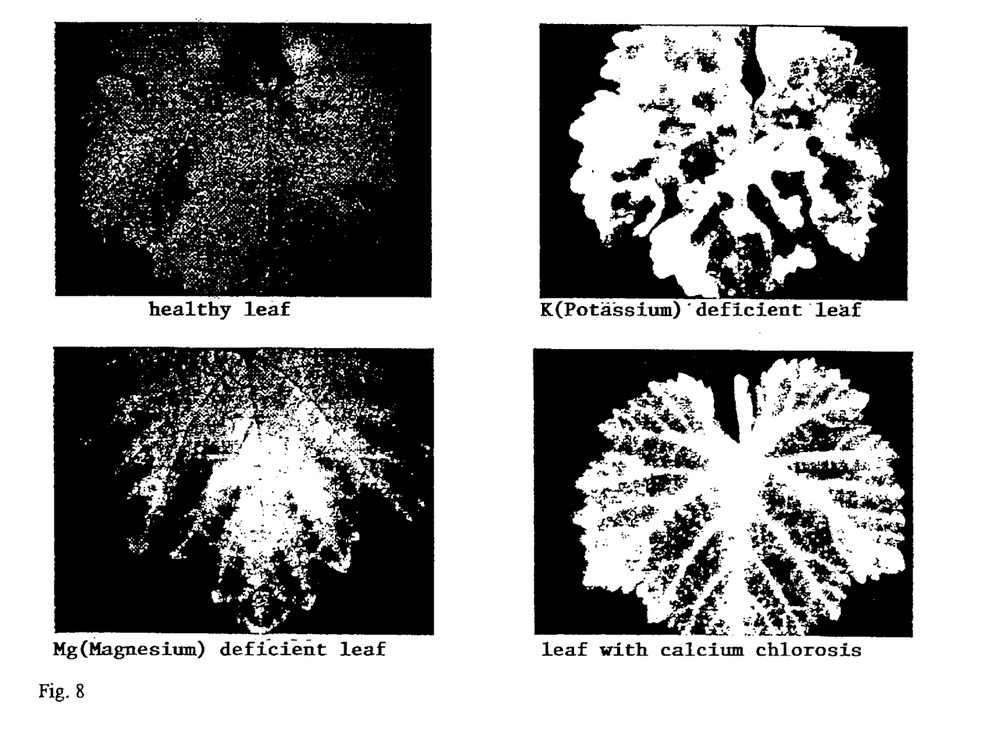

FIG. 8 shows fluorescence images obtained from grape leaves, respectively healthy, deficient in potassium, deficient in magnesium and afflicted with calcareous chlorosis.

These images were taken at 690 nm, with an excitation laser of 532 nm.

It will be seen from an observation of these images that potassium deficiency can be characterized by the appearance of very irregular fluorescence patches of different intensities and that magnesium deficiency can be characterized by greater fluorescence at the center of the leaf and rapidly decreasing in intensity toward the edge of this latter.

It will also be noted that in the case of calcareous chlorosis, the ribs are very fluorescent relative to the rest of the leaf.

Figure 9:
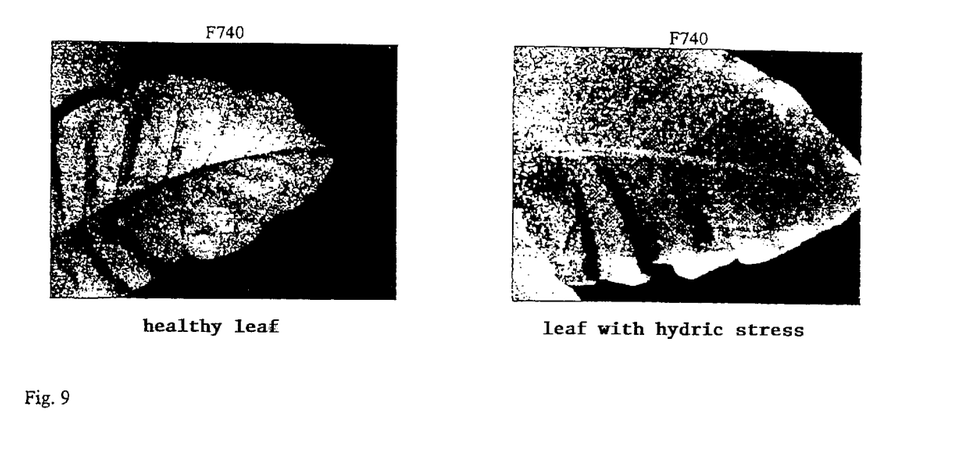

FIG. 9 shows fluorescence images obtained from tobacco leaves, respectively in good health and having hydric stress.

These images were taken at 740 nm, with an excitation laser of 355 nm.

These images show clearly a greater fluorescence at the edge of the stressed leaf, constituting a preliminary drying symptom of the leaf, whilst no difference is visible between the two leaves in question to the naked eye.

Figure 10:
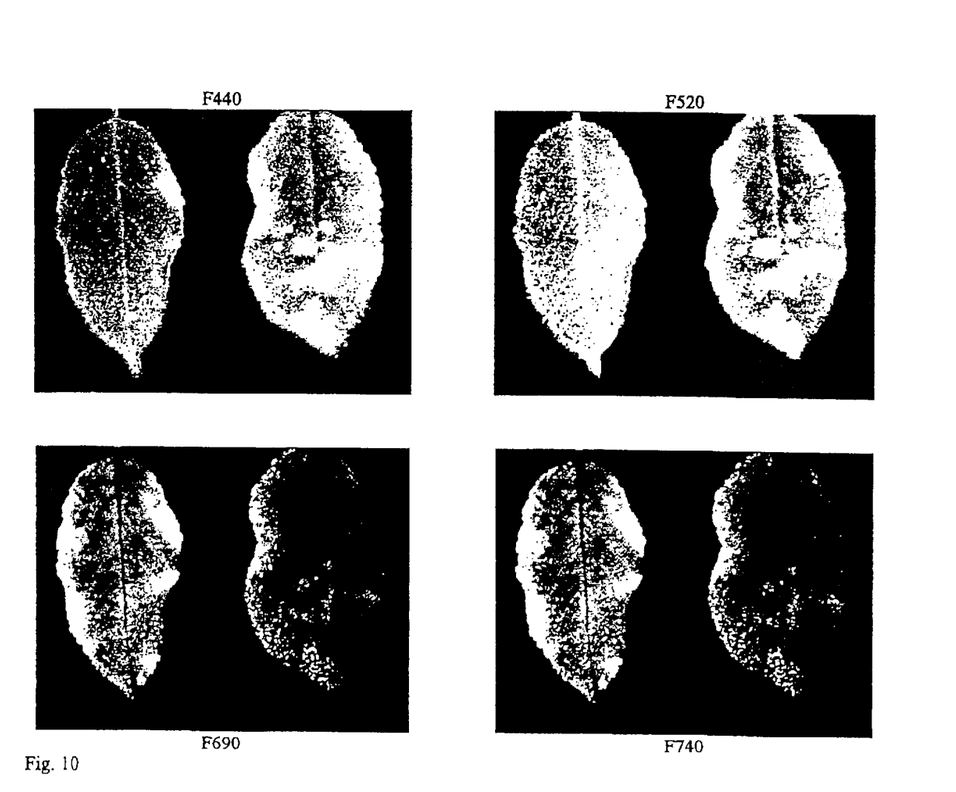

FIG. 10 shows fluorescence images obtained from leaves of an apple tree with an excitation laser of 355 nm and taken at four emission wavelengths characteristic of the plants (F440=440 nm, F520=520 nm, F690=690 nm, F740=740 nm).

In each image, the left leaf has been exposed to sun during its growth and the right leaf has been exposed to the north during its growth.

It will be noted that on the F690 and F740 images, the edges of the leaf exposed to the sun or to the south are more fluorescent than those of the leaf exposed to the north, which indicates hydric stress and more advanced maturity.

Figure 11:
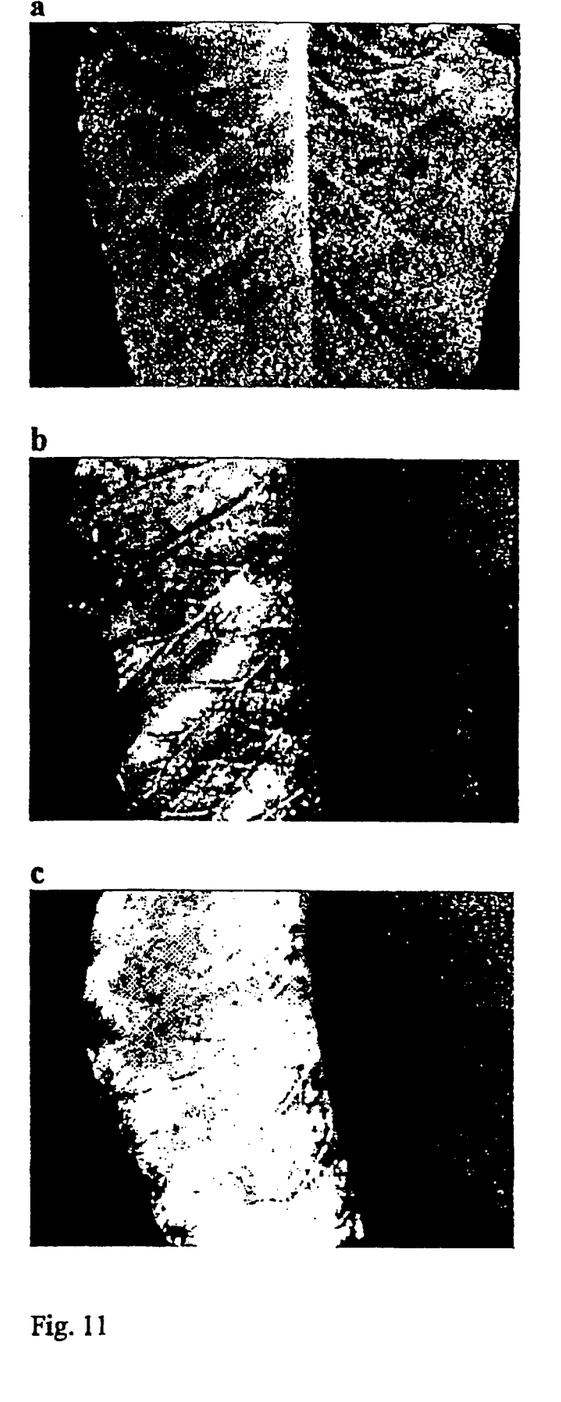

FIG. 11 shows fluorescence images obtained from a tobacco leaf subjected to treatment with a herbicide DCMU: 3-(3,4 Dichlorophenyl-1,1-dimethylurea) by surface spraying.

The three images of this figure have been taken at 690 nm, with an excitation laser of 355 nm.

The images a, b and c show respectively a healthy leaf before treatment, the same leaf treated by spraying over its left half on the rear surface and analyzed after 10 minutes, then 30 minutes, after application of the herbicide.

It will be noted from these images that there is a large increase of chlorophilic fluorescence in the treated portion of the leaf (no change visible to the naked eye), indicating a blockage of the photosynthesis mechanism of the leaf in this portion).

Of course, the invention is not limited to the embodiments described and shown in the accompanying drawings. Modifications remain possible, particularly as to the construction of the various elements or by substitution of technical equivalents, without thereby departing from the scope of protection of the invention.

What is claimed is:

1. A device for the non-destructive analysis of plants, comprising:
    a laser emitter that simultaneously emits at least two laser beams with different wavelengths including at least an ultraviolet wavelength and a green wavelength;
    a first unit for taking images of fluorescence emitted by plants irradiated by laser beams from said laser emitter, said first unit comprising means for forming at least two secondary beams with different wavelengths from one fluorescent beam emitted by the irradiated plants, an obturator/light intensifier, and a matrix sensor, each of the secondary beams constituting a separate fluorescence image in said matrix sensor;
    a synchronization circuit for synchronizing operation of said laser emitter, said matrix sensor, and said obturator/light intensifier; and
    a second unit for digitally processing, storing, and editing the fluorescence images.

2. The device of claim 1, wherein said means for forming forms the two secondary beams sequentially.

3. The device of claim 1, wherein said means for forming forms the two secondary beams simultaneously.

4. The device of claim 1, wherein one of the laser beams emitted by said laser emitter has a wavelength of 380 to 390 nm and another of the laser beams emitters by said laser emitter has a wavelength of 560 to 600 nm.

5. The device of claim 1, wherein said obturator/light intensifier comprises interference filters that are selectively brought into a path of the one fluorescent beam.

6. The device of claim 1, wherein said means for forming forms four secondary beams with different wavelengths from the one fluorescent beam, each of the four secondary beams constituting a separate fluorescence image in a different portion of said matrix sensor.

7. The device of claim 1, wherein said synchronization circuit correlates durations of laser pulses from said laser emitter and durations of opening said obturator/light intensifier with each other.

8. The device of claim 1, wherein said first unit forms the fluorescence images by summing a plurality of comparative images that are formed by subtracting two consecutive images, one with laser irradiation and one without laser irradiation.

9. A device for the non-destructive analysis of plants, comprising:
    a laser emitter that simultaneously emits at least two laser beams with different wavelengths including at least an ultraviolet wavelength and a green wavelength;
    a first unit for taking images of fluorescence emitted by plants irradiated by laser beams from said laser emitter, said first unit comprising means for forming at least two secondary beams with different wavelengths from one fluorescent beam emitted by the irradiated plants, an obturator/light intensifier, and a CCD camera whose operation is correlated with said obturator/light intensifier, each of the secondary beams constituting a separate fluorescence image in said CCD camera;
    a second unit for digitally processing, storing, and editing the fluorescence images; and
    a synchronization circuit comprising a burst signal generator correlated with by said CCD camera, an adjustable delay line that is correlated with said burst signal generator and that provides a trigger signal to said laser emitter, a control. generator that receives a trigger input from said adjustable delay line and that triggers said obturator/light intensifier, wherein said adjustable delay line adjusts a timing of the trigger input to said control generator as a function of a distance between the device and a plant being irradiated by said laser emitter.

10. A vehicle carrying a device for the non-destructive analysis of plants,
    wherein the device comprises;
        a laser emitter that simultaneously emits at least two laser beams with different wavelengths including at least an ultraviolet wavelength and a green wavelength, a first unit for taking images of fluorescence emitted by plants irradiated by laser beams from said laser emitter, said first unit comprising means for forming at least two secondary beams with different wavelengths from one fluorescent beam emitted by the irradiated plants, an obturator/light intensifier, and a matrix sensor, each of the secondary beams constituting a separate fluorescence image in said matrix sensor, a synchronization circuit for synchronizing operation of said laser emitter, said matrix sensor, and said obturator/light intensifier, and a second unit for digitally processing, storing, and editing the fluorescence images; and wherein the vehicle comprises a telescoping beam on which said device is movably carried.

11. The vehicle of claim 10, wherein said telescoping beam movably carries said device between a first position outside the vehicle where said device analyzes plants in situ and a second position inside the vehicle where said device analyzes plants within the vehicle.

* * * * *